(12) United States Patent
Leung et al.

(10) Patent No.: US 11,898,127 B1
(45) Date of Patent: Feb. 13, 2024

(54) HARVESTING CELL-BASED MEAT

(71) Applicant: Upside Foods, Inc., Berkeley, CA (US)

(72) Inventors: Matthew Leung, Richmond, VA (US); Konrad Müller-Auffermann, Emeryville, CA (US)

(73) Assignee: Upside Foods, Inc., Berkeley, CA (US)

( * ) Notice: Subject to any disclaimer, the term of this patent is extended or adjusted under 35 U.S.C. 154(b) by 0 days.

(21) Appl. No.: 17/935,334

(22) Filed: Sep. 26, 2022

(51) Int. Cl.
*C12M 3/00* (2006.01)
*A23J 3/04* (2006.01)
*C12N 5/077* (2010.01)
*A22C 17/00* (2006.01)

(52) U.S. Cl.
CPC ......... *C12M 21/08* (2013.01); *A22C 17/0006* (2013.01); *A23J 3/04* (2013.01); *C12N 5/0652* (2013.01)

(58) Field of Classification Search
None
See application file for complete search history.

(56) References Cited

U.S. PATENT DOCUMENTS

| 2014/0154745 | A1  | 6/2014 | Zijlstra et al. | |
| 2016/0206664 | A1* | 7/2016 | Sokal | A61K 35/407 |
| 2021/0198635 | A1  | 7/2021 | Tanabe et al. | |
| 2022/0079194 | A1* | 3/2022 | Li | B33Y 80/00 |

FOREIGN PATENT DOCUMENTS

| CN | 215799616 U | 2/2022 |
| CN | 114653702 A | 6/2022 |
| FR | 3101522 A1 | 4/2021 |
| WO | WO 2021/207293 A1 | 10/2021 |

OTHER PUBLICATIONS

Arshad et al., Cogent Food & Agriculture (2017), 3: 1320814, 11 pages (Year: 2017).*
Navarro et al., Biotechnol Bioeng. Dec. 2019; 116(12): 3253-3268 (Year: 2019).*
Rajwani et al., Food Safety Magazine, published May 31, 2022, 5 pages (Year: 2022).*
WIPO English Machine Translation of CN 215799616 (Year: 2022).*
Good Meat, Dossier in Support of the Safety of Good Meat Cultured Chicken as a Human Food Ingredient, 155 pages ; retrieved from the internet https://www.fda.gov/media/166346/download (Year: 2022).*
Humbird et al., Biotechnol Bioeng: 2021;118:3239-3250 (Year: 2021).*
WayBack Machine Archive for Good Meat FDA Submission Mar. 4, 2022 public availability online: https://www.fda/gov/media/166346/download (Year: 2023).*
International Search Report & Written Opinion as received in PCT/US2022/077014 dated Dec. 8, 2022.

* cited by examiner

*Primary Examiner* — Evelyn Y Pyla
(74) *Attorney, Agent, or Firm* — Keller Preece PLLC

(57) ABSTRACT

This disclosure describes methods for growing cells in a controlled environment in a growing room, transporting the cells to a harvest room, and removing the cells from the controlled environment in the harvest room. The disclosed method can limit exposure of cells to contaminants by maintaining a controlled environment through cell growth and additional processing. For instance, the cells may be washed and cooled within the controlled environment. The cells are transferred to a harvest room where they are harvested and removed from the controlled environment.

20 Claims, 10 Drawing Sheets

Cooling Solutions

HARVESTING CELL-BASED MEAT

BACKGROUND

As the world's population continues to grow, cell-based or cultured meat products for consumption have emerged as an attractive alternative (or supplement) to conventional meat from animals. For instance, cell-based, cultivated, or cultured meat represents a technology that could address the specific dietary needs of humans. Cell-based meat products can be prepared from a combination of cultivated adherent and suspension cells derived from a non-human animal. Because the cells for cell-based meat are made in a food cultivation facility, cell masses are often formed and shaped to mimic familiar forms of conventional meat.

In addition to addressing dietary needs, cell-based-meat products help alleviate several drawbacks linked to conventional meat products for humans, livestock, and the environment. For instance, conventional meat production involves controversial practices associated with animal husbandry, slaughter, and harvesting. Other drawbacks associated with harvested or slaughtered meat production include low conversion of caloric input to edible nutrients, microbial contamination of the product, emergence and propagation of veterinary and zoonotic diseases, relative natural resource requirements, and resultant industrial pollutants, such as greenhouse gas emissions and nitrogen waste streams.

Despite advances in creating cell-based-meat products, existing methods or systems for cultivating and processing cell-based-meat products face several shortcomings, such as challenges or failures in controlling contamination and other inefficiencies. Existing methods for producing cell-based-meat products are subject to contamination. For example, existing methods often grow and process cells using methods that expose cells to contaminants. Some contaminants can proliferate and further contaminate cell-based meat samples.

In addition to contamination, existing systems typically form cell-based meats with limited shelf life. In one example, comestible cell-based meat products fall within the jurisdictions of several regulatory bodies (e.g., the Food and Drug Administration and/or the Department of Agriculture). Different regulatory bodies have their own rules, protocols, and operational hours. Existing methods are typically inefficient in passing comestible cell-based-meat products through regulatory jurisdictions. For example, existing methods use excessive amounts of time waiting to pass from one regulatory jurisdiction to another. Inefficiencies in passing comestible cell-based-meat products through regulatory jurisdictions often limits the time the cell-based-meat products may be on the shelf or the viability of the cells.

These, along with additional problems and issues exist in existing methods for cultivating cell-based-meat products.

BRIEF SUMMARY

This disclosure generally describes methods and apparatuses for growing and processing cells in a controlled environment before harvesting the cells. For example, the disclosed method includes growing cells in a bioreactor/cultivator in a controlled environment. The cells can be transferred to a harvest collector within the controlled environment. The disclosed method may comprise moving the harvest collector from a growing room to a harvest room. The cells may be removed from the controlled environment in the harvest room. Generally, the disclosed method limits the exposure of both adherent cells and cells grown in suspension to air outside the controlled environment before harvest.

Additional features and advantages of one or more implementations of the present disclosure will be set forth in the description that follows.

BRIEF DESCRIPTION OF THE DRAWINGS

Various implementations will be described and explained with additional specificity and detail through the use of the accompanying drawings, which are summarized below.

DETAILED DESCRIPTION

Figure 1:
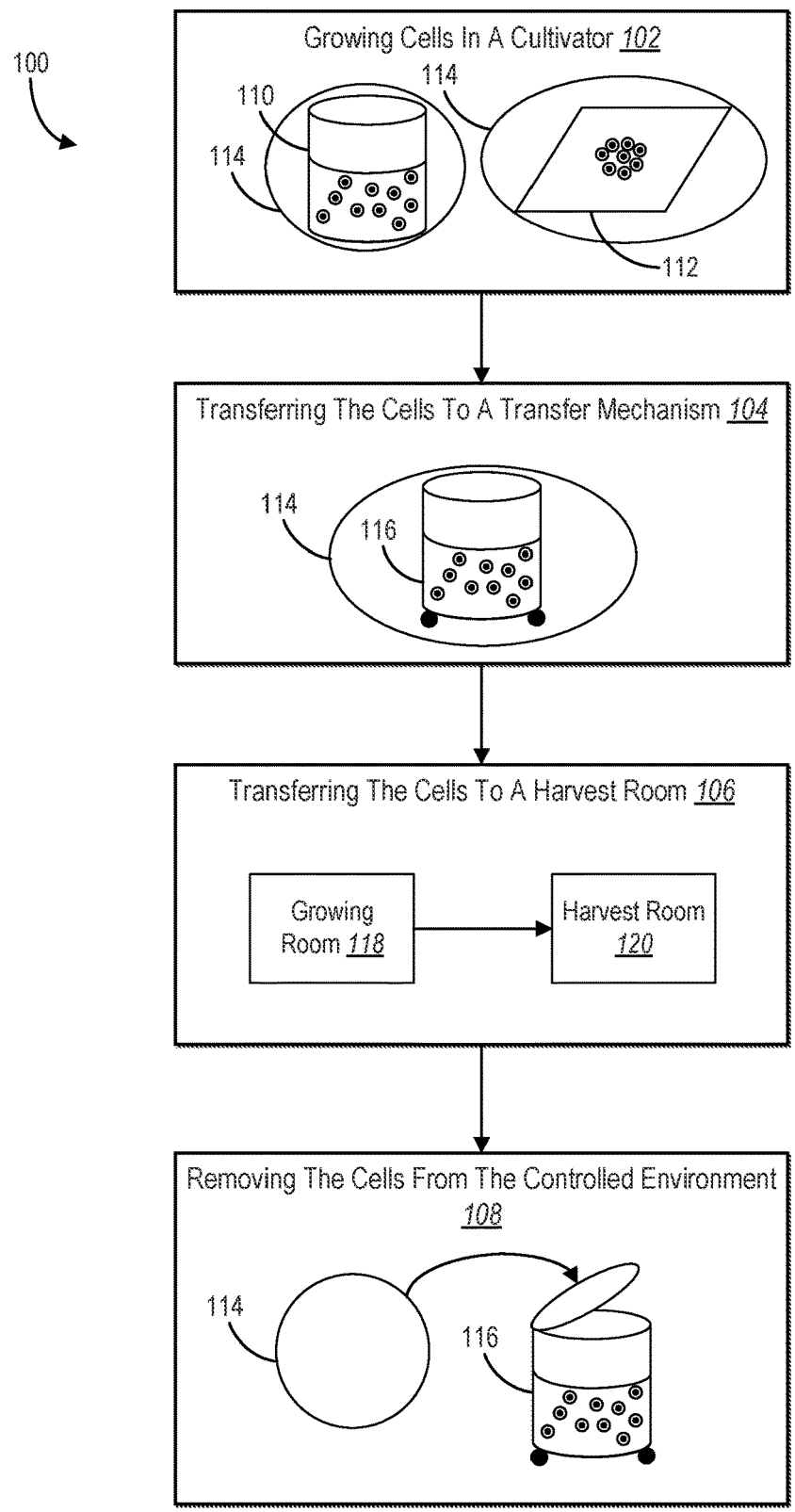
FIG. 1 illustrates an overview diagram of growing cells in a controlled environment, transporting the cells to a harvest room, and removing the cells from the controlled environment in the harvest room in accordance with one or more implementations of the present disclosure.

This disclosure describes one or more implementations of a method for growing and processing cells in a controlled environment before harvesting the cells. In one or more implementations, the disclosed method comprises growing cells in a cultivator and removing the cells from the cultivator through fully controlled means. The disclosed method further comprises processing the cells and transferring them to a transportable chamber in the controlled environment. The chamber can be moved to a transition or harvest room where the cells are removed from the controlled environment. For instance, the cells are first exposed to air in the harvest room.

To illustrate, in some implementations, the disclosed method comprises growing cells in a cultivator within a controlled environment. In some implementations, the cultivator is housed within a growing room. The disclosed method also includes moving the cells from the growing room to a harvest room while maintaining the controlled environment. The cells are removed from the controlled environment in the harvest room.

As mentioned, the disclosed method comprises growing cells in a cultivator within a controlled environment. The cultivator may be housed within a growing room. Cells may be grown in suspension or as adherent cells within a cultivator such as a bioreactor. Cell culture media is circulated through the cultivator to stimulate the growth and proliferation of the cells within the cultivator.

The disclosed method further includes moving the cells from the growing room to the harvest room while maintaining the controlled environment. In particular, the disclosed method utilizes a transfer mechanism to transport the cells. More specifically, the cells are removed from the cultivator through fully controlled means and without exposing the cells to external air or any external environment. In one example, the meat cells are transferred into an enclosed harvest collector through fully enclosed means, therefore resulting in the maintenance of the sterile envelope until at such time the raw material is subject to further processing or storage and would be removed from the sterile envelope. The harvest collector can comprise a closed vessel used for transporting the cells.

The cells may be further processed within the controlled environment. In particular, at least a portion of the cell culture media can be removed from the cells in the controlled environment. The cells may also be cooled and washed in the controlled environment. In some examples, enrichment media is added to the cells within the controlled environment. In one or more implementations, the cells are processed in the controlled environment of a transfer mechanism (e.g., a harvest collector).

As mentioned, the cells are moved to a harvest room. In particular, the cells are transferred from a growing room to the harvest room via a transfer mechanism. In some instances, the growing room and the harvest room are connected by an equipment-only door to reduce cross contamination. The cells are harvested in the harvest room and removed from the controlled environment.

The disclosed method provides several benefits relative to existing methods for growing cell-based meats. In particular, the disclosed method keeps cells within a controlled environment through growth and processing. More specifically, by maintaining a controlled environment, the disclosed method limits, both in terms of space and time, potential external contamination of the cells until harvest and thereby reduces contamination risk. Furthermore, by limiting contact between the cells and ambient air, the disclosed method limits the proliferation of aerobic contaminants in the cells. In some instances, vacuum may be used to reduce air pressure during one or more steps of the method disclosed herein to further reduce aerobic contamination. In some instances, sterile filtered air may be used to increase air pressure during one or more steps of the method disclosed herein to further reduce ingress of external air into the controlled environment.

Additionally, the disclosed method extends the shelf life of cell-based meats. More specifically, by washing, cooling, and enriching cells before harvest, the disclosed method limits spoilage time and reduces contamination risk for the cells. Furthermore, the disclosed method improves efficiency of inspection by different regulatory bodies. To illustrate, by separating a growing room and a harvest room, the disclosed method may create a clean split between jurisdictions of the FDA and USDA within a cell-based-meat production plant. A separation of locational jurisdictions will reduce delays that would occur under jurisdictional duplicity.

As illustrated by the foregoing discussion, the present disclosure utilizes a variety of terms to describe features and advantages of the disclosed method. Additional detail is now provided regarding the meaning of such terms. As used herein, the term "cells" refers to cells that are useful for forming a cell-based meat product for consumption. Generally, cells may comprise non-human mesenchymal progeny. For instance, cells may comprise at least one of muscle cells, muscle progenitor cells, or muscle support cells. In particular, cells may comprise different cell types, such as one or more of myoblasts, mesangioblasts, myofibroblasts, mesenchymal stem cells, hepatocytes, fibroblasts, pericytes, adipocytes, epithelial, chondrocytes, osteoblasts, osteoclasts, pluripotent cells, somatic stem cells, endothelial cells, or other similar cell types. Furthermore, cells may comprise different types of progenitor cells, including myogenic progenitors, adipogenic progenitors, mesenchymal progenitors, or other types of progenitor cells. In some instances, the cells may comprise cells from distinct lineages, such as ectoderm or endoderm lineages, that have been transdifferentiated into cells useful for forming a cell-based meat product for consumption, such as those cell types described above.

As used herein, the term "cell mass" refers to a tissue or mass of cells. Cell mass refers to cells of cultivated meat gathered into a collective mass. In some implementations, the cell mass is comestible. Additionally, a cell mass can include grown cells that have been nourished by a growth medium to grow during a formation period within a cultivator. In some examples, a cell mass is grown from cells attached to a substrate in an adherent reactor.

As used herein, the term "cultivator" refers to a vessel used for culturing cells. In particular, a cultivator refers to an environment that can hold cells and cell culture media. For example, a cultivator can include an adherent reactor system that contains a substrate for growing adherent cells. Additionally, a cultivator can include a substrate-free bioreactor system for growing cells in suspension.

As used herein, the term "suspension culture" (or "suspension") refers to cells growing in an at least partially liquid growth medium in which cells grow, multiply, and/or maintain nourishment. In particular, a suspension includes an agitated growth medium that is housed in a container in which single cells or small aggregates of cells grow, multiply, and/or maintain nourishment from the nutrients of the agitated growth medium. Cells grown in suspension are not attached to a substrate and therefore differ from a conventional adherent culture.

As used herein, the term "controlled environment" refers to a space with regulated environmental factors. In particular, a controlled environment includes a space in which certain parameters, such as pressure, temperature, and segregation, are controlled. More specifically, external contaminants are limited, or nonexistent, within a controlled environment. For instance, a controlled environment is isolated from contaminants found in air (e.g., ambient air). For example, a controlled environment may comprise an environment with sterile air flow that acts as a barrier to protect cells from external contaminants or an enclosed environment. More specifically, a controlled environment can comprise a biosafety cabinet that blows sterile air to act as a barrier to reduce or prevent contamination, a laminar flow hood designed to maintain a sterile environment by drawing air in, or transport mechanism across which sterile air is flowed to reduce or prevent contamination. An "enclosed environment" comprises an area that is contained on all sides. In particular, an enclosed environment includes one or more fluidly connected spaces that are at least substantially closed off from external contaminants. In another example, a controlled environment comprises a transfer mechanism, such as a series of sterile containers including a cultivator and a harvest collector. The series of containers may be sterilized and sealed prior to receiving cells. In another example, a controlled environment comprises a series of pipes for transporting and processing cells.

As used herein, the term "harvest" or "harvesting" refers to a process of removing cells from a controlled environment. For example, harvesting refers to the process of removing cells from a controlled environment and exposing them to air. Harvesting may comprise removing adherent cells or suspension cells from a controlled environment. In one or more implementations, harvesting comprises opening a harvest collector holding cells, wherein the cells are exposed to air (e.g., ambient air, filtered air, and/or refrigerated air) and any contaminants therein.

More specifically, harvesting cells can occur, in one or more implementations, when the cells are removed from the cultivator (e.g., bioreactor). In particular, harvesting occurs when removing the cells from the cultivator involves removing the cells from a controlled environment or exposing the cells to air. Alternatively, the cells are removed from the cultivator (e.g., bioreactor) without removing the cells from the controlled environment such that harvesting takes place after the cells are removed from the cultivator.

Along similar lines, harvesting cells can occur, in one or more implementations, when the cells are separated from a cell culture media (e.g., growth or nutrient media). In particular, when separating the cells from the cell culture media involves removing the cells from a controlled environment or exposing the cells to air, harvesting occurs. Alternatively, the cells are separated from a cell culture media before removing the cells from the controlled environment such that harvesting takes place after the cells are separated from a cell culture media.

As used herein, the term "transfer mechanism" refers to a system of one or more parts used to transport cells from one location to another. In particular, a transfer mechanism refers to an apparatus for transporting cells from one location to another within a controlled environment. For example, a transfer mechanism may comprise a container such as a harvest collector. In another example, a transfer mechanism comprises a system of one or more apparatus that together transport cells to a harvesting room. To illustrate, a transfer mechanism may comprise a depositor that deposits cells into a sterilized vacuum tube, a conveyor belt with a forced air flow, a tube-delivery system that transfers the vacuum tube into a harvest room all while maintaining a controlled environment, or some combination thereof.

As used herein, the term "harvest collector" refers to a container for holding and transporting cells. In particular, a harvest collector comprises a sealed container that holds cells pre-harvest and optionally different media for transfer into a harvest room. For example, a harvest collector may comprise a vessel that holds cells and one or more of cell culture media, wash buffer, enrichment media, or other media and buffers. A harvest collector is fluidly connectable to a cell cultivator. In particular, in one or more implementations, cells are grown in a cell cultivator and transferred to a harvest collector without removing the cells from a controlled environment or exposing the cells to air. For example, once the cells are within the harvest collector, a fluid connection connecting the harvest collection and the cell cultivator can be disconnected and sealed, thereby enabling the harvest collector to move from a room with the cell cultivator to another room without exposing the cells to air.

As used herein, the term "harvest room" refers to a room in which cells are harvested. In particular, a harvest room is where cells are exposed to external air or otherwise removed from a controlled environment. For example, a harvest room may comprise a clean room having a low concentration of airborne particulates in a cell-based-meat processing facility. In another example, the harvest room comprises ambient air, filtered air, refrigerated air, or some combination thereof. In some implementations, the US Department of Agriculture (USDA) has locational jurisdiction over the harvest room.

As used herein, the term "growing room" refers to a room in which cells are grown and processed. In particular, a growing room contains a cultivator and other vessels for proliferating and processing the cells. For instance, cells may be washed, cooled, enriched, and moved into a harvest collector in the growing room. Furthermore, in some implementations, the cells are inspected for safety and/or quality before moving into the harvest room. In some implementations, the US Food and Drug Administration (FDA) has locational jurisdiction over the growing room. The FDA may further have jurisdiction over weighing and dispensing cell culture media, media milling, some warehouse, and cold storage rooms.

Additional detail will now be provided regarding disclosed method in relation to illustrative figures portraying example implementations and implementations of the disclosed methods. FIG. 1 illustrates an overview of growing cells in a controlled environment in a first location and removing the cells from the controlled environment in a second location. By way of overview, FIG. 1 illustrates a series of acts 100 comprising an act 102 of growing cells in a cultivator, an act 104 of transferring the cells to a transfer mechanism, an act 106 of transferring the cells to a harvest room, and an act 108 of removing the cells form the controlled environment.

FIG. 1 illustrates the act 102 of growing cells in a cultivator. The act 102 comprises growing cells in a cultivator within a controlled environment. The cultivator may house suspension cells 110 or adherent cells 112 in a controlled environment 114. As mentioned, the suspension cells 110 comprise cells grown in cell culture media. In some examples, the cultivator includes agitators for agitating the cell culture media. A cultivator may also grow the adherent cells 112. Generally, adherent cells grow into a cell mass when attached to a substrate within an adherent reactor. The cultivator may circulate cell culture media over substrates to nourish the cell mass and remove waste products.

FIG. 1 further illustrates the act 104 of transferring the cells to a transfer mechanism. The act 104 comprises moving the cells from the cultivator into a transfer mechanism within the controlled environment. As illustrated in FIG. 1, the cells are transferred to a harvest collector 116 within the controlled environment 114. As mentioned previously, the controlled environment 114 comprises a space that is at least substantially closed off from external contaminants, such as contaminants found in air (e.g., ambient air). The following paragraphs describe example implementations for performing the act 104 of transferring the cells from the cultivator to a transfer mechanism within the controlled environment.

In one example, the act 104 comprises transferring the cells from the cultivator into the harvest collector 116 by fluidly securing the harvest collector 116 to the cultivator and flowing the cells into the harvest collector 116. In such an example, the transfer mechanism comprises the harvest collector 116 and apparatus used to connect the cultivator to the harvest collector 116. In another example, the act 104 comprises transferring the cells from the cultivator into the harvest collector 116 by opening a valve controlling fluid communication between the cultivator and the harvest collector, wherein the cells may flow from the cultivator to the harvest collector while remaining enclosed. In some implementations, to ensure that the harvest collector 116 provides a satisfactory controlled environment 114 isolated from contaminants, the harvest collector 116 is sterilized and sealed prior to receiving the cells. The sterilized and at least substantially air-tight harvest collector 116 is attached to the cultivator. The harvest collector 116 may be directly attached to an outlet of the cultivator or connected to the cultivator via pipes or tubes that together comprise the transfer mechanism. The pipes and tubes may also be sterilized prior to connecting to the cultivator.

In a small-scale example, the act 104 comprises transferring the cells into a transfer mechanism by moving the cells from the cultivator into a sterilized harvest collector within a sterile hood or bio safety cabinet. The sterile hood is part of the controlled environment 114 because it maintains a sterile environment and limits exposure of the cells to contaminants.

Figure 2:
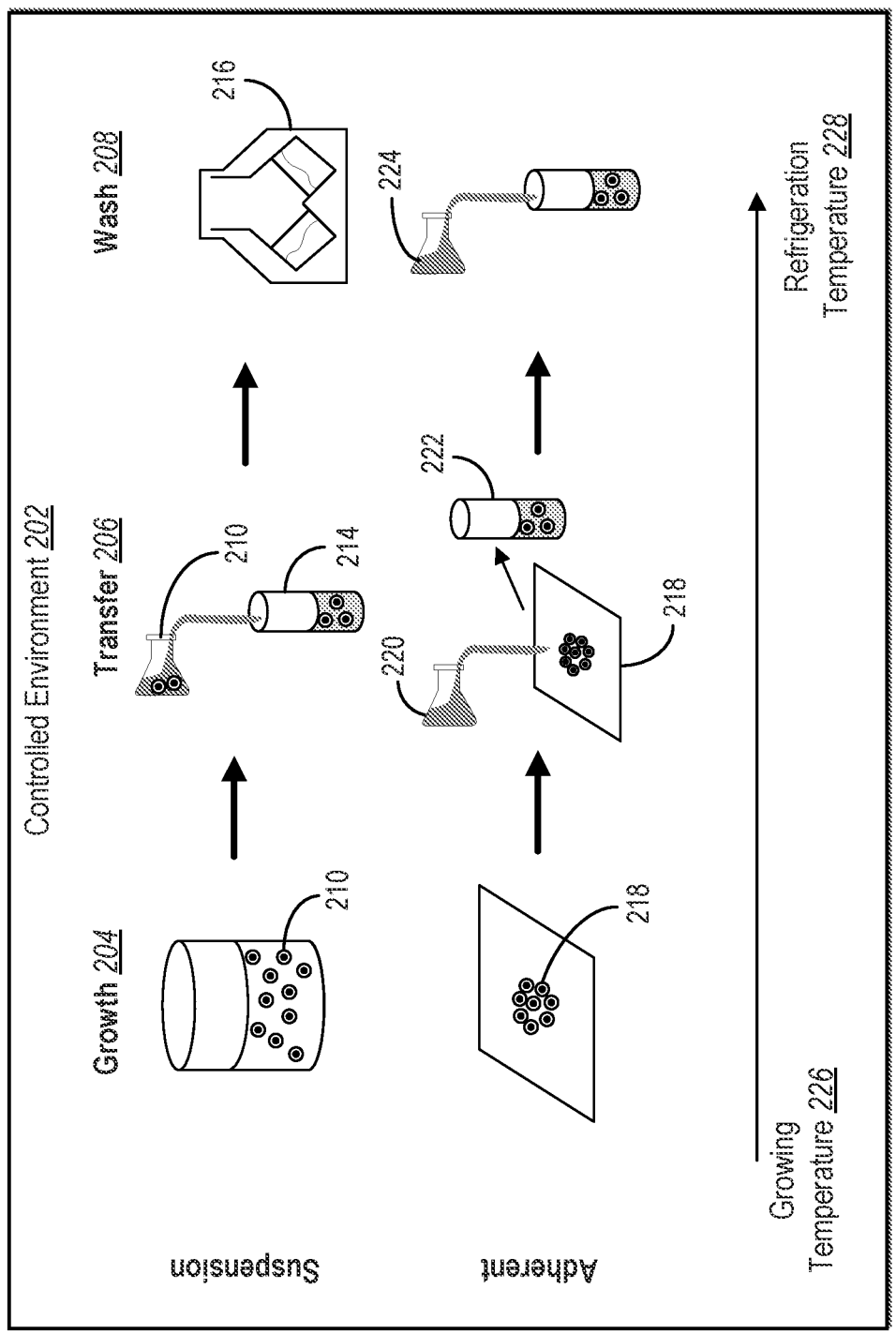
FIG. 2 illustrates cooling cells at different phases within the controlled environment in accordance with one or more implementations of the present disclosure.
Figure 3:
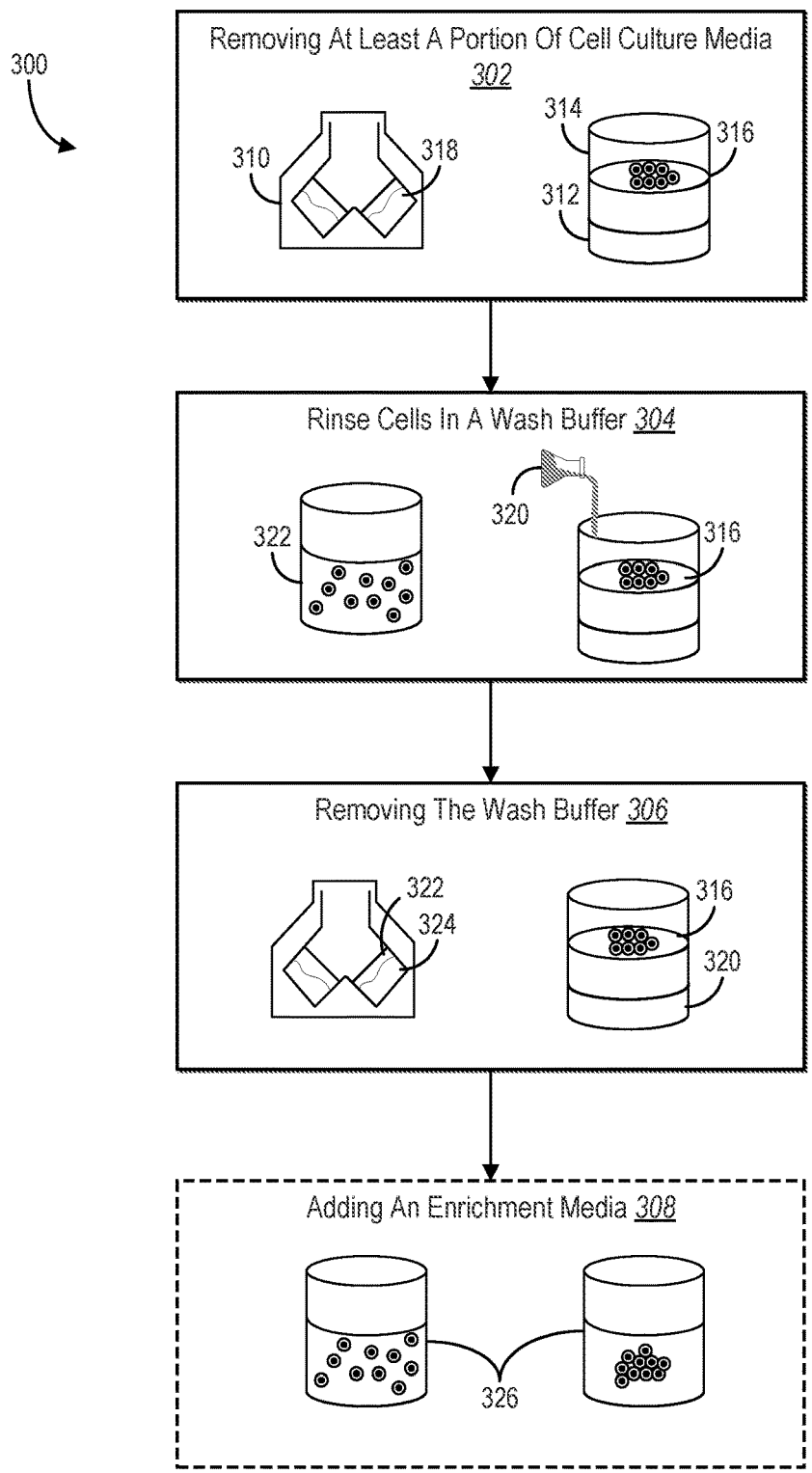
FIG. 3 illustrates washing the cells in accordance with one or more implementations of the present disclosure.

In some implementations, the series of acts 100 includes an additional act of processing the cells within the controlled environment 114. More specifically, the disclosed method may include cooling, washing, and/or enriching the cells. The disclosed method may include cooling, washing, and/or enriching the media before, during, and/or after transferring the cells to the harvest collector 116. FIG. 2 and the corresponding discussion further detail cooling the cells in accordance with one or more implementations. FIG. 3 illustrates washing and enriching the cells in accordance with one or more implementations.

Figure 5:
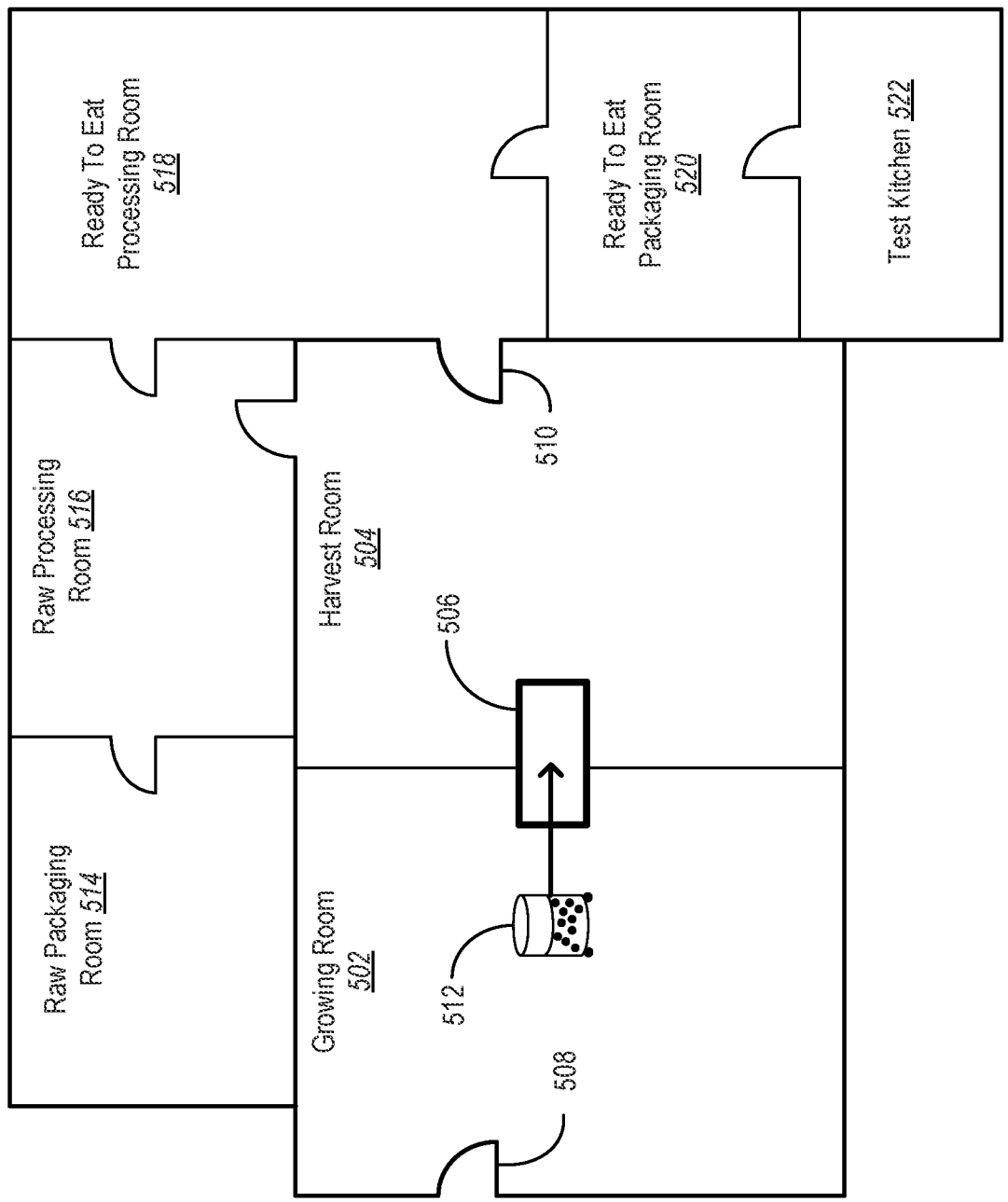
FIG. 5 illustrates an example growing room and harvest room in accordance with one or more implementations of the present disclosure.

FIG. 1 further illustrates the act 106 of transferring the cells to a harvest room. As illustrated, the act 106 comprises moving the cells from a growing room 118 to a harvest room 120 using the transfer mechanism. During moving, the transfer mechanism remains in the controlled environment. For instance, the harvest collector 116 remains at least substantially sealed and/or airtight as the harvest collector moves into the harvest room 120. FIG. 5 and the corresponding paragraphs further detail the movement of the cells into the harvest room 120 in accordance with one or more implementations. In other embodiments, the cells are moved from the growing room 118 into the harvest room 120 through other transfer mechanisms, such as a fixed apparatus capable of transporting the cells without damaging their structural integrity, e.g. a conveyor belt or low flow piping, in an at least substantially sealed and/or airtight manner.

The series of acts 100 illustrated in FIG. 1 includes the act 108 of removing the cells from the controlled environment. In particular, the act 108 comprises removing the cells from the controlled environment 114 in the harvest room 120. In some implementations, removing the cells from the controlled environment 114 comprises exposing the cells to air (e.g., ambient air, filtered air, and/or refrigerated air). Cells can be within a controlled environment even when oxygen or other gases are flowed over the cells. For instance, cells within a biosafety cabinet with oxygen or other gases flowed over them are still considered to be within a controlled environment. For instance, the act 108 may comprise opening or breaking the seal of the harvest collector 116 to expose the cells to contaminants found in ambient air.

In some examples, the act 108 of removing the cells from the controlled environment comprises separating the cells from cell culture media. For example, in the case of suspension cells, the cells are harvested when the cells are separated from cell culture media by centrifugation. The cells may be further washed with a wash buffer to further remove cell culture media from the cells. In the case of adherent cells, the cells are harvested when cell culture media is drained from the cultivator. In some implementations, harvest is not complete until remnant cell culture media is removed by rinsing the cells using a wash buffer. Additionally, or alternatively, harvest is not complete until liquid, including wash buffer, saline solution, and/or enrichment media is at least partially removed from the cells. For instance, the cells may be pressed, centrifuged, filtered, or otherwise dried to remove liquid from the cells.

As mentioned, in one or more implementations, the disclosed method comprises processing the cells by cooling the cells in the controlled environment. Generally, in such implementations, the disclosed method cools the cells after growing and before harvest. FIG. 2 illustrates cooling the cells within a controlled environment 202 in accordance with one or more implementations. More specifically, FIG. 2 illustrates cooling suspension cells and adherent cells.

By way of overview, FIG. 2 illustrates growth phase 204, transfer phase 206, and a wash phase 208 of suspension cells and adherent cells. Suspension cells 210 are grown suspended in cell culture media in the cultivator. During the transfer phase 206, the suspension cells 210 are moved to a harvest collector 214. Suspension cells 210 may be centrifuged to adjust moisture content before, during, or after transfer to the harvest collector 214. The cells may be washed in the wash phase 208 using a wash buffer. For instance, a wash buffer may be added to the cells. The wash buffer cell mixture is spun in a centrifuge 216 to separate the cells and the wash buffer. In some implementations, the wash buffer is removed and an enrichment media added to the cells during an enrichment phase. FIG. 3 and the corresponding paragraph provide additional detail regarding washing and enriching the suspension cells in accordance with one or more implementations.

As illustrated in FIG. 2, cell mass 218 are grown on a substrate within an adherent reactor. During the transfer phase 206, a cell media 220 may be sprayed or otherwise flowed across the substrate to release the cell mass 218 from the substrate into a harvest collector 222. The fluid pressure from the cell media 220 may encourage the release of the cell mass 218 from the substrate. The cell media 220 can comprise cell culture media drained from the cultivator and re-cycled into the cultivator or may comprise a wash buffer. The cell mass may be further washed during the wash phase 208 using a wash buffer 224. FIG. 3 and the corresponding paragraph provide additional detail regarding washing and enriching the cell mass in accordance with one or more implementations. In some implementations, to maintain sterility of the controlled environment, the cell media 220 and wash buffer are sterilized and/or pasteurized before use.

Additionally, or alternatively, the disclosed method comprises using an automated scraping mechanism to release the cell mass 218 from a substrate. More specifically, a cell scraper may be drawn across the substrate to release the cell mass 218 from the substrate and into the cell culture media. The cell culture media and the released cells are drained from the cultivator into the harvest collector 222. The cell media 220 may be flowed over the substrate to move any remaining cells or cell clusters into the harvest collector 222.

As illustrated in FIG. 2, the disclosed method comprises cooling cells from a growing temperature 226 to a refrigeration temperature 228. By cooling the cells before removing them from the controlled environment 202 (i.e., harvest), the disclosed method dramatically limits the growth of undesirable microbes in or on the cells. On the other hand, cultivators typically maintain higher temperatures to stimulate growth and proliferation in cells. The growing temperature 226 comprises any temperature suitable for growing cells. For instance, the growing temperature 226 can be in a range of 44 F-211 F. In some implementations, the growing temperature 226 is below 44 F or above 211 F.

In some examples, the growing temperature 226 is about 95 F. However, keeping the cells at the growing temperature 226 after the growth phase may also stimulate the growth of other cells comprising undesirable contaminants. Typically, microbes may grow in a range of 40 F-140 F. Microbes may introduce toxins and other substances in comestible cell-based-meat products that may reduce edibility and/or palatability. Accordingly, the disclosed system comprises cooling the cells and/or their environment to the refrigeration temperature 228. In some implementations, the cells are cooled to refrigeration temperatures in accordance with USDA and/or FDA regulations. The disclosed system can comprise cooling the cells before, during, or after removing the cells from the controlled environment 202. In some implementations, the refrigeration temperature 228 comprises a temperature below the growing temperature. For example, the refrigeration temperature 228 can be a temperature below room temperature. In some examples, the refrigeration temperature 228 is within a range of 32 F-55 F. More specifically, in one or more implementations, the disclosed method comprises cooling the cells to a temperature between 32 F-44 F before, during, and/or after moving the harvest collector to the harvest room, wherein successful proliferation of cells, cells or otherwise, is reduced or eliminated.

Figure 4:
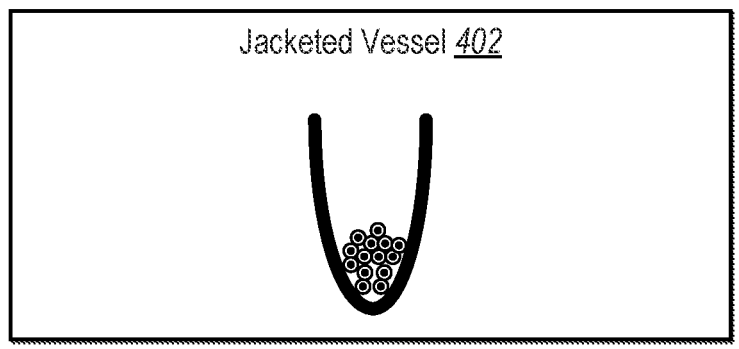
FIG. 4 illustrates various cooling methods in accordance with one or more implementations of the present disclosure.
Figure 4:
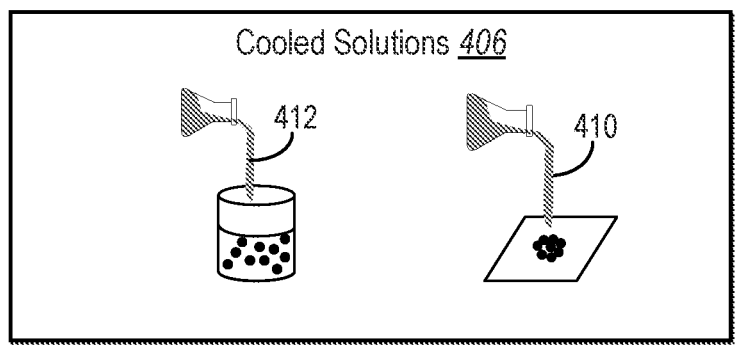
Figure 4:
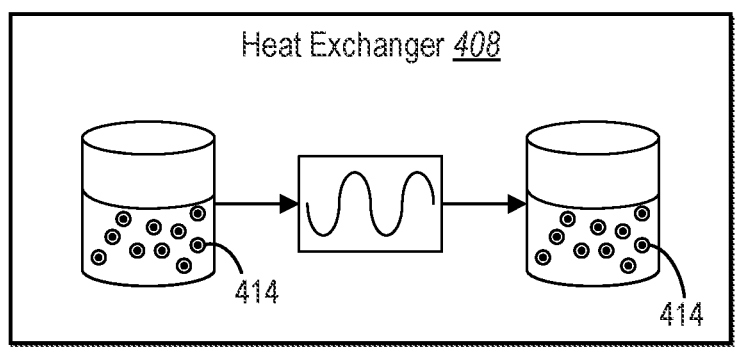

As illustrated in FIG. 2, the disclosed method may cool the cells at various phases within the controlled environment 202. The disclosed method may cool cells at the transfer phase 206, the wash phase 208, or an enrichment phase. For example, during transfer of the cell mass 218, the disclosed method may comprise spraying the substrate with a cooled cell media 220. As used herein cooled cell media 220 refers to media that has a temperature lower than the temperature of the cell mass 218. In one or more implementations, the cell culture media may be drained from the cultivator, cooled in a cooling vessel, then sprayed or flowed onto the substrate in the cultivator. In another example, the harvest collector 214 and the harvest collector 222 may comprise cooled vessels. For instance, the harvest collector 214 and the harvest collector 222 can comprise jacketed vessels. In other examples, the cells are washed during the wash phase 208 with a cooled wash buffer. Additionally, or alternatively, the cells may be stored in a cooled enrichment media. FIG. 4 and the accompanying paragraphs further detail specific cooling methods used in the different phases.

In some implementations, the disclosed method comprises cooling the cells during transfer to the harvest room. To illustrate, in some implementations, the cells are transferred to a jacketed harvest collector. The jacket on the harvest collector cools the cells as they are being moved from the growing room into the harvest room. In another example, a cooled enrichment media is added to the harvest collector before moving the harvest collector to the harvest room. Thus, cells may be cooled as they are moved into the harvest room.

Additionally, or alternatively, the disclosed method comprises cooling or continuing to cool the cells after harvest. In one example, the cells are cooled but not quite to the refrigeration temperature 228 prior to harvest. For instance, the cells may be cooled to an intermediate temperature (e.g., 50 F-60 F) before harvest. After harvest, the cells are further cooled to the refrigeration temperature 228. For example, the harvest room is kept at refrigeration temperatures, and the cells are cooled to meet the refrigeration temperatures over time. In some implementations, the cells are cooled from the growing temperature 226 to the refrigeration temperature 228 after harvest. FIG. 4 and the corresponding discussion further detail different methods used to cool the cells in accordance with one or more embodiments.

In addition to cooling the cells before harvest, the disclosed method can optionally comprise the processes of washing and enriching the cells prior to harvest. FIG. 3 illustrates a series of acts 300 for washing and enriching suspension cells and adherent cells (or a cell mass) in accordance with one or more implementations. By way of overview, FIG. 3 illustrates a series of acts 300 including an act 302 of removing at least a portion of cell culture media, an act 304 of rinsing cells in a wash buffer, an act 306 of removing the wash buffer, and an act 308 of adding an enrichment media. The series of acts illustrated in FIG. 3 may occur during or after harvest. For instance, in some implementations, harvest comprises separating cells from cell culture media. In other instances, the cells are washed after removal from the controlled environment in the harvest room.

The series of acts 300 illustrated in FIG. 3 includes the act 302 of removing at least a portion of cell culture media. For cells grown in suspension, the disclosed method can separate cells 318 from cell culture media by utilizing a centrifuge 310. For example, the disclosed method comprises draining the cells and cell culture media from a cultivator into one or more harvest collectors. The one or more harvest collectors are placed within the centrifuge 310 and spun to separate the cells 318 and the cell culture media. The cell culture media may be poured off, aspirated, or otherwise removed from the cells 318.

For adherent cells, the disclosed method may perform the act 302 of removing at least a portion of the cell culture media by utilizing a filter. The filter drains excess moisture from the cell mass. As mentioned, in some implementations, a cell mass is dislodged from the substrate by fluid pressure from the substrate by flowing cell culture media or a saline solution over the substrate. The disclosed method filters the cell culture media to separate the cells and remove the cell culture media. For example, and as illustrated in FIG. 3, the disclosed method comprises flowing cell culture media 312 and the cell mass from the cultivator into a harvest collector 314 having a filter 316. The cell culture media 312 flows through the filter 316 while the cells are captured by the filter 316. In some small-scale operations, the filter 316 comprises a mesh bag. Furthermore, in some implementations, the disclosed method separates suspension cells from cell culture media by utilizing the filter 316.

FIG. 3 also illustrates the act 304 of rinsing cells in a wash buffer. Generally, the disclosed method rinses cells in a wash buffer to remove residual cell culture media on the cells. As illustrated in FIG. 3, the act 304 comprises resuspending the cells in a wash buffer 322. In some implementations, the cells and wash buffer 322 mixture is agitated by shaking the harvest collector. In another example, the harvest collector contains an agitator for agitating the cells and the wash buffer 322.

For adherent cells and, in some instances, suspension cells, the disclosed method performs the act 304 of rinsing the cell mass by pouring a wash buffer 320 over the filter 316 holding the cells. To illustrate, the wash buffer 320 can be flowed over the cell mass resting on the filter 316. In some embodiments, the wash buffer 320 is recirculated over the cell mass. In other embodiments, the wash buffer 320 is flowed over or through the cell mass once and discarded.

FIG. 3 further illustrates the act 306 of removing the wash buffer. For cells grown in suspension, the disclosed method removes the wash buffer 322 from washed cells 324 by centrifuging the wash buffer 322 and the washed cells 324.

In some examples, the wash buffer 322 and the washed cells 324 are centrifuged in the centrifuge 310 used to remove the cell culture media. The wash buffer 322 is drained, aspirated, or otherwise removed from the washed cells 324. The wash buffer 322 is removed from the washed cells 324 in the controlled environment.

In some implementations, the disclosed method comprises removing the wash buffer until the cells meet a desired moisture content. More specifically, certain cell-based-meat products may correspond with specific moisture content. The act 306 can comprise simply draining the wash buffer from the cells. Additionally, or alternatively, the disclosed method further comprises drying the cells. For example, the cells may be filtered, vacuum dried, or spray dried to meet a specific moisture content prior to harvest.

For adherent cells the act 304 of removing the wash buffer comprises flowing the wash buffer 320 through the cells and the filter 316. The adherent cells are captured by the filter 316 and the runoff buffer contains few to no cells. In some implementations, the disclosed method further comprises draining or otherwise removing the wash buffer 320 from the harvest collector 314.

The disclosed method may comprise any number of washes. To illustrate the disclosed method may comprise repeating the act 304 and the act 306 more than one time. The wash buffer used in successive washes may have the same or different makeups. For example, the wash buffer used to rinse the cells can transition from a composition similar to the cell culture media to a composition more similar to an enrichment media (e.g., high in antioxidants and having a high pH for color and taste adjustments). For instance, the disclosed method comprises washing the cells 3-4 times. In another example, the cells are washed in a continuous single wash where the wash buffer changes composition over time.

As further illustrated in FIG. 3, the series of acts 300 may include an additional act 308 of adding an enrichment media. Generally, for both suspension cells and adherent cells, the additional act 308 comprises adding enrichment media 326 to the harvest collector. The enrichment media 326 includes additives that enhance organoleptic properties of the cells including taste, appearance, texture, and smell. For cells washed using a filter, the filter 316 may be lowered to immerse the cells or cell mass in the enrichment media 326. Additionally, or alternatively, enough enrichment media 326 is added to immerse the cells resting on the filter 316.

In some implementations, the disclosed method further comprises reducing liquid or moisture content of the cells before and/or after moving them to the harvest room. In particular, the disclosed method comprises centrifuging cells, filtering the cells, pressing the cells, or otherwise removing liquid from the cells prior to harvest. For example, in some implementations, either the wash buffer or the enrichment media is removed by centrifuging cells grown in suspension. For adherent cells, the harvest collector can include a filter that allows excess moisture to drain away from the cell mass.

In addition, or in the alternative, to washing and enriching the cells before harvest, the disclosed method comprises washing and enriching the cells after harvest. In particular, in some implementations, one or more of the acts 302-308 are performed outside of the controlled environment. In one example where all the acts 302-308 are performed after harvest, the disclosed method comprises moving the cells from the cultivator into the harvest room. For instance, the disclosed method comprises transferring the cells to a harvest collector and moving the harvest collector to a harvest room. The harvest collector is opened in the harvest room to expose the cells to air. Cell culture media is removed from the cells and the cells are washed in the harvest room. In another example, some of the acts illustrated in FIG. 3 are performed after harvest and outside of the controlled environment. For instance, cell culture media may be removed from the cells and the cells are washed in the controlled environment. The cells may be removed from the controlled environment (for instance, within the harvest room) and enrichment media added to the cells.

Furthermore, in some implementations, the disclosed method comprises repeating one or more of the acts 302-308 outside of the controlled environment. For instance, the disclosed method may comprise performing the acts 302-308 within the controlled environment and repeating the acts 304-308 outside of the controlled environment.

As mentioned previously, in one or more implementations, the disclosed method uses different cooling methods to cool the cells before harvest. FIG. 4 illustrates various cooling methods in accordance with one or more implementations. By way of overview, FIG. 4 illustrates a jacketed vessel 402, cooled solutions 406, and a heat exchanger 408. The disclosed method may utilize one or a combination of the illustrated cooling methods.

FIG. 4 illustrates the jacketed vessel 402. The disclosed method may cool the cells by transferring the cells from the cultivator into harvest collector within a jacketed vessel. In some implementations, the harvest collector comprises the jacketed vessel 402. For example, cells and cell culture media from a cultivator can be transferred into a harvest collector comprising a jacketed bag filter. Generally, the jacketed vessel 402 is a container designed for draining fluid and/or controlling the temperature of its contents by using a cooling jacket around the vessel. Cooling fluids are circulated through the jacketed vessel 402.

FIG. 4 also illustrates cooling cells using the cooled solutions 406. The cooled solutions 406 comprise cooled media or buffers that contact and cool the cells. For instance, the disclosed method may include washing cells with a cooled wash buffer 412. Additionally, or alternatively, the disclosed method may include using cooled cell culture media 410 to release adherent cells from a substrate. In some implementations, adherent cells are released from the substrate using a cooled saline solution. As mentioned, the disclosed method may drain cell culture media from the cultivator, cool the cell culture media, and circulate or spray the cooled cell culture media 410 over the substrate to release the cells from the substrate. In another example, the disclosed method utilizes a cooled cell media beside cell culture media to release the cells from the substrate. Additionally, in some implementations, the cooled solutions 406 includes cooled enrichment media. For instance, the disclosed method comprises adding a cooled enrichment media to the cells before harvesting the cells.

The cooled solutions 406 may be at different temperatures. Generally, the cooled solutions 406 are at a temperature that is cooler than the growing temperature. For instance, if the growing temperature equals 95 F, then the cooled solutions 406 are a temperature below 95 F and at or equal to a final refrigeration temperature. In some implementations, the cooled solutions 406 are at a temperature below the refrigeration temperature. For example, the cooled solutions 406 may be below refrigeration temperatures to quickly cool the cells to refrigeration temperatures. Additionally, or alternatively, the disclosed method comprises using several cooled solutions at incrementally colder temperatures to gradually cool the cells. For instance, the disclosed method may include releasing cells from the substrate using cell culture media at room temperature, washing cells with a wash buffer or a saline solution at a cooled temperature (e.g., 65F, 75 F, etc.), and storing the cells using enrichment media at refrigeration temperatures (e.g., 44 F). In another example, the cells are rinsed using a series of progressively colder wash buffers or saline solutions. For instance, the cooled solutions can be at temperatures of 80F, 70 F, 60 F, etc.

As further illustrated in FIG. 4, the disclosed method may cool the cells using the heat exchanger 408. The heat exchanger 408 is a system used to transfer heat between different fluids. The disclosed method may efficiently cool the cells by utilizing the heat exchanger 408. As illustrated, the disclosed method may comprise passing cells 414 through the heat exchanger 408 to cool the cells 414. In some implementations, the disclosed method comprises use of the heat exchanger 408 in conjunction with an energy storage tank. The energy storage tank improves efficiency of cell growing and processing by storing liquids that may be used to both cool and heat fluids. For example, the heat exchanger may use heat from the cells 414 to warm liquid in an energy storage tank. The warmed liquid from the energy storage tank may be utilized to warm cell culture media for growing future batches of cells.

As mentioned previously, in some implementations, the cells are cooled completely, or in part, after harvest. To illustrate, in some embodiments, the cells are stored in a jacketed vessel in the harvest room. Additionally, the disclosed method may comprise adding cooled solutions to the cells after harvest. For example, in some implementations, the cells are washed with a cooled wash buffer after harvest. In another example, cooled enrichment media is added to the cells after harvest. Furthermore, a heat exchanger may be used in the harvest room to cool cells after harvest. More particularly, the heat exchanger may be used in conjunction with the jacketed vessel to form a complete cooling/heating system. Additionally, the harvest room is kept at refrigeration temperatures. Thus, in some implementations, the disclosed method comprises cooling the cells after harvest by exposing the cells to cooled ambient air, filter air, and/or refrigerated air in the harvest room. In yet another implementation, cells are pressed after harvest. The cell press may comprise cooled surfaces that, when in contact with the cells, efficiently cool the cells.

As mentioned, cells are grown and processed within a controlled environment in a growing room and removed from the controlled environment in a harvest room. FIG. 5 illustrates a layout of a growing room 502, a harvest room 504, a raw packaging room 514, a raw processing room 516, a ready to eat processing room 518, a ready to eat packaging room 520, and a test kitchen 522 in accordance with one or more implementations. FIG. 5 illustrates an equipment-only door 506 connecting the growing room 502 and the harvest room 504. By clearly defining a room for growing and processing cells (e.g., the growing room 502) and a room for harvesting cells (e.g., the harvest room 504), the disclosed method can also clearly define jurisdictions of regulatory bodies. While FIG. 5 illustrates a single growing room, the disclosed method may utilize a plurality of growing rooms. For instance, the cultivator may be in a first growing room and additional processing may occur in a second growing room.

FIG. 5 illustrates the growing room 502. The growing room 502 comprises an area housing a cultivator. Cells may be transferred from the cultivator to a harvest collector 512 in the growing room 502. Processing steps, including cooling, washing, and adding enrichment media to the harvest collector 512, occur in the growing room 502. In some implementations, the growing room 502 comprises a hygienically designed room. The growing room 502 includes a growing room door 508 that serves as an entrance and exit for the growing room 502. In some implementations, the growing room 502 is kept at room temperature (e.g., 68 F-72 F).

The growing room 502 may be associated with cleanliness protocols. In one example, the growing room 502 falls within the jurisdiction of the US FDA. Accordingly, protocols within the growing room 502 are dictated by the US FDA. For instance, people entering the growing room door 508 must comply with safety and hygiene precautions corresponding with the growing room 502. For instance, people within the growing room 502 must wear hair nets and captive shoes.

As illustrated by FIG. 5, the growing room 502 and the harvest room 504 are separated by an equipment-only door 506. The equipment-only door 506 only allows passage of the air-tight harvest collector 512 directly from the growing room 502 to the harvest room 504. In some implementations, the equipment-only door 506 is not just one door but several to prevent cross-contamination between the growing room 502 and the harvest room 504. People may not pass directly from the growing room 502 to the harvest room 504. A person traveling from the growing room 502 to the harvest room 504 must first exit the growing room 502 using growing room door 508. The person must enter the harvest room 504 using a harvest room door 510. In some implementations, a person may only enter the harvest room door 510 after adhering to a set of safety precautions specific to the harvest room 504 to minimize the bioburden on the final cell-based meat product. For example, a person entering the harvest room door 510 may be required to follow special gowning procedures that include caps, shoe covers, gloves, hoods, masks, coveralls, goggles, and others. Additionally, persons entering the harvest room door 510 may be required to undergo other cleanliness procedures including, but not limited to, washing hands, sanitizing clothing, or other procedures.

In some embodiments, the equipment-only door 506 may be replaced or supplemented with a fixed apparatus that allows for the transfer of cells from a cultivator to the harvest room. In some instances, the transfer of cells from the cultivator to the harvest room is performed in an automated, sealed, and sterile manner while maintaining the structural integrity of the cells, e.g. a low flow pipe or a conveyor belt. In one or more examples, the growing room 502 and the harvest room 504 are connected by a connection pipe or a series of connection pipes. The connection pipe is part of the controlled system and is used to transport the cells and/or media from the growing room 502 to the harvest room 504. Thus, instead of transporting the cells by moving the harvest collector 512 from the growing room 502 to the harvest room 504, the disclosed method can comprise moving the cells by simply piping the cells from the growing room 502 to the harvest room 504. In some implementations, the connection pipe is used to transport cells grown in suspension but not adherent cells. More specifically, adherent cells typically grow to form cell masses or cellular tissue. Tissue cell products are more difficult to transport via connection pipes because the cellular tissue grows in contiguous multicellular masses (e.g., clumps, sheets, tubes, and other shapes). The shape, structure, and texture of the contiguous multicellular masses may clog connection pipes.

As such, adherent cells may be more efficiently transferred by a conveyor belt or by a similar belt driven mass transfer apparatus. In one example, the adherent cells may be transferred to the harvest room 504 via agar or screw driven delivery, a vacuum tube, or transferred via a transfer mechanism (e.g., a harvest collector) within a controlled environment. More specifically, the cells may be transferred to a harvest collector that is belted into the harvest room 504 where the harvest collector is opened. In some embodiments, the cells are moved to the harvest room 504 during USDA inspection hours (e.g., 6:30 am-2 pm).

FIG. 5 illustrates the harvest room 504. Generally, cells are removed from a controlled environment in the harvest room 504. For example, the harvest collector 512 is opened for the first time in the harvest room 504. In some implementations, the harvest room 504 comprises a wash down room. The interior surfaces of the harvest room 504 may be made of an easy to clean material such as stainless steel. Tables and other equipment in the harvest room 504 may also be made of the same material. Additionally, the ambient temperature in the harvest room 504 may be refrigeration temperature (e.g., 35 F-44 F). In one or more examples, the harvest room 504 falls under USDA jurisdiction. More specifically, the cells are transferred to USDA jurisdiction upon harvest or when the harvest collector 512 is opened and the cells are removed from the controlled environment. In some implementations, the harvest room 504 comprises a clean room having a low concentration of airborne particulates.

In some implementations, the disclosed method comprises filtering air entering the growing room 502 and the harvest room 504. More specifically, the disclosed method uses dedicated filters for each of the growing room 502 and the harvest room 504 to avoid cross contamination. The air in the growing room 502 and the harvest room 504 is thus filtered.

Cells harvested in the harvest room 504 may undergo additional processing either within the harvest room 504 or in other rooms. For instance, the harvest collector 512 is opened in the harvest room 504 and the cells further moisture adjusted and/or dried. The moisture adjusted and/or dried cells are then transported from the harvest room 504 into the raw processing room 516. Raw cells are processed in the raw processing room 516. For example, the cells can be combined with additives (e.g., spices, food stabilizers, etc.) and otherwise processed in the raw processing room 516. Processed raw cells may be transferred to the raw packaging room 514 for packaging. In some implementations, the USDA has jurisdiction over the raw processing room 516, as well as any additional warehouse, cold storage, and spice rooms.

In some implementations, instead of packaging a raw cellular-based product for distribution, the disclosed method comprises cooking or otherwise preparing the cell-based-meat product so it is ready to eat. Cells can be further prepared for consumption in the ready to eat processing room 518. For example, cooked cell-based-meat products can be flavored, cut, shaped, or otherwise processed in the ready to eat processing room 518. In some embodiments, raw product is moved from the raw processing room 516 into the ready to eat processing room 518 where it is cooked. Processed ready-to-eat product is further moved into the ready to eat packaging room 520 for packaging. In some implementations, the USDA has jurisdiction over the raw processing room 516, the ready to eat processing room 518, and the ready to eat packaging room 520.

FIG. 5 illustrates the test kitchen 522. Raw or ready to eat products may be tested in the test kitchen 522. For example, the cell-based-meat products may be inspected and tested for safety and quality in the test kitchen 522.

While FIG. 5 illustrates an example layout of various rooms for growing and harvesting cells, other layouts are possible. For example, the disclosed method may utilize more or fewer rooms for transitioning and/or processing cell-based-meat product.

Additionally, while FIG. 5 illustrates the growing room 502 and the harvest room 504 as neighboring rooms within a facility, the growing room 502 and the harvest room 504 may exist in separate facilities. For example, the cells may be grown and processed in the growing room 502 and stored in a fully controlled harvest collector 512 in the growing room 502. The harvest collector 512 may then be transferred to an outside facility for harvest and additional processing.

Figure 6A:
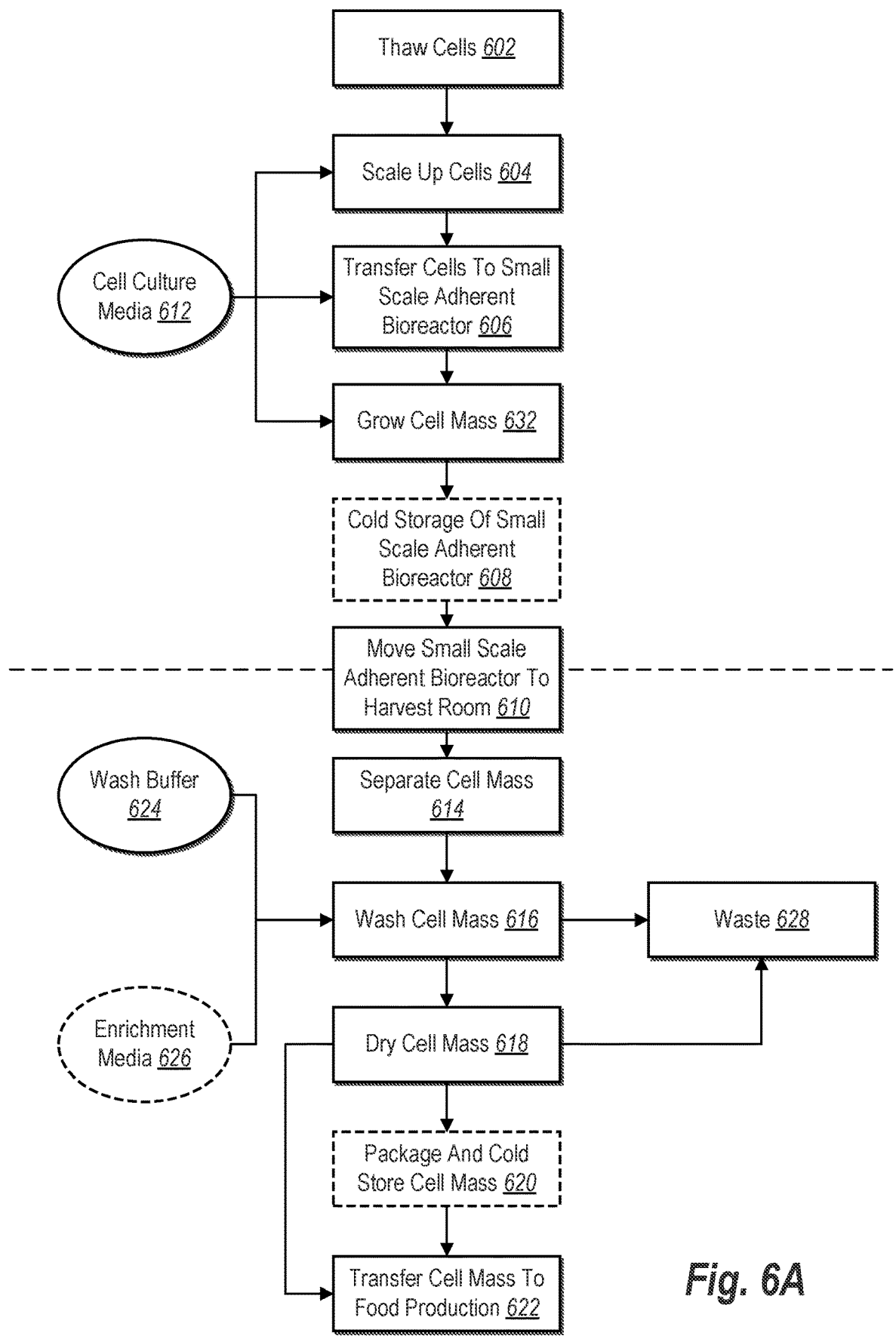
FIGS. 6A-6B illustrate example series of acts for small-scale and large-scale growth and harvest of cells in accordance with one or more implementations of the present disclosure.
Figure 6B:
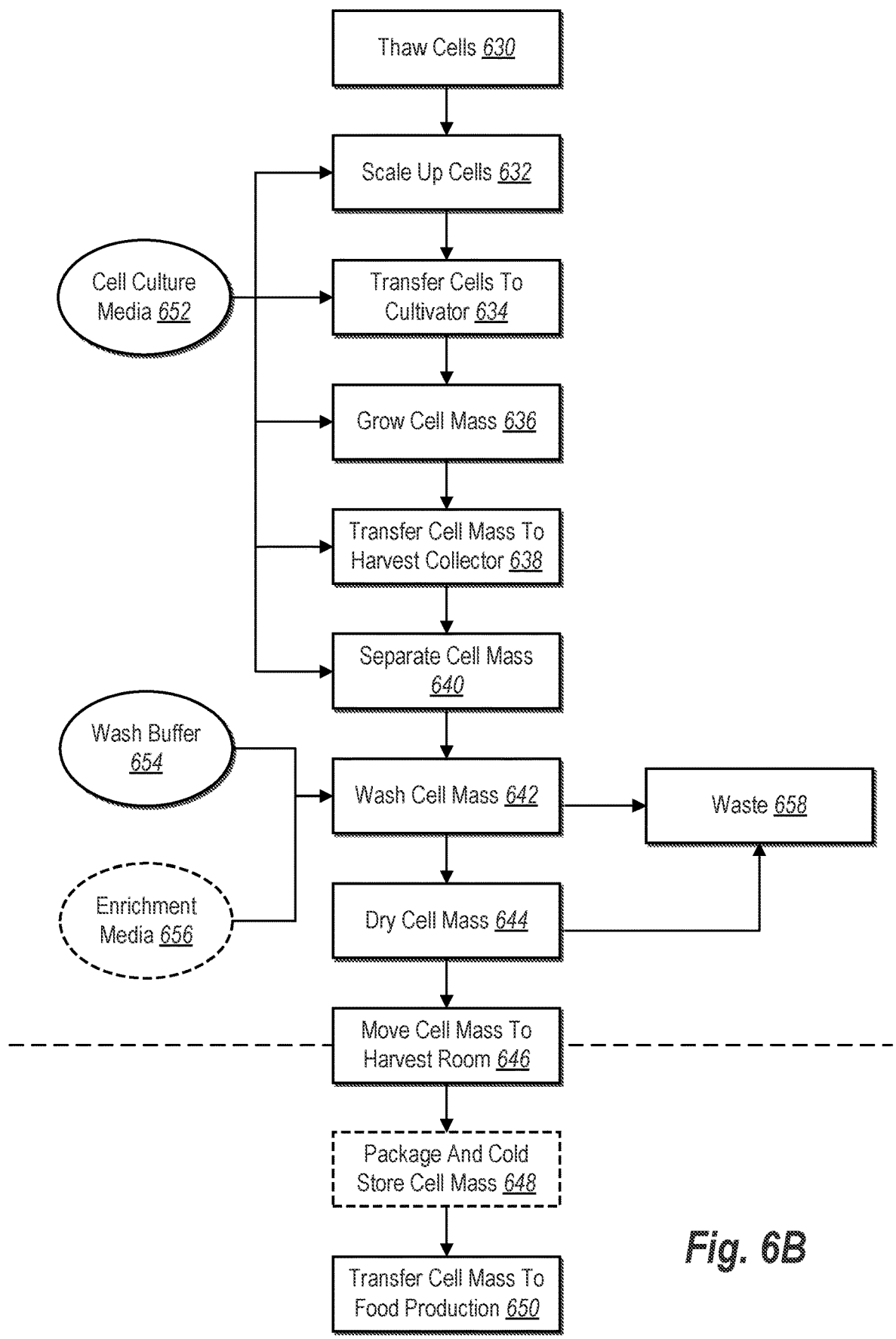

The disclosed method can be used to grow and harvest adherent cells at different scales. FIGS. 6A-6B illustrate overviews growing and harvesting adherent cultures at a small scale and a large scale, respectively. Generally, small-scale cellular growth refers to growth of one or more cell masses of limited volume. For example, small-scale cellular growth can be used to form limited volumes of cell masses for research and development purposes. For instance, during small-scale cellular growth, cells are grown within a small scale adherent bioreactor. In contrast, large-scale cellular growth refers to growth of cell masses of production volume. For example, large-scale cellular growth forms cell masses by growing them in large bioreactors.

FIG. 6A illustrates an example small-scale cellular growth process in accordance with one or more embodiments. FIG. 6A illustrates an act 602 of thawing cells and an act 604 of scaling up cells. In some embodiments, the act 604 comprises passaging and scaling up cells in preparation for seeding. For instance, passaging and scaling the cells may comprise moving the cells and cell culture media 612 into larger containers to provide additional room for cellular growth. The act 604 of scaling up the cells may continue until the cells reach a target population doubling time.

FIG. 6A further includes an act 606 of transferring cells to a FIG. 6A further illustrates the act 632 of growing the cell mass in the small scale adherent bioreactor. More specifically, the cells grow and proliferate to form cellular tissue. While growing the cellular mass, the disclosed method comprises adding the cell culture media 612 and other necessary reagents to feed the cell mass.

In some implementations, the disclosed method comprises an optional act 608 of cold storage of the small scale adherent bioreactor. In some implementations, the small scale adherent bioreactor and its contents (e.g., the cell mass and the cell culture media 612) are cooled. For example, the small scale adherent bioreactor may be stored within a refrigerator or a cooling bath.

As illustrated in FIG. 6A, the disclosed method comprises an act 610 of moving the small scale adherent bioreactor to the harvest room. As illustrated, acts below the dashed line occur in the harvest room. More specifically, acts that follow the act 610 may be performed after removing the cell mass from the controlled environment. In some implementations, the act 610 may be performed after different acts. For instance, in some implementations, the act 610 of moving the small scale adherent bioreactor to the harvest room is performed after the act 616 of washing the cell mass.

FIG. 6A further illustrates the disclosed method comprising an act 614 of separating the cell mass as part of harvesting the cell mass. In some implementations, separating the cell mass refers to separating the cell culture media from the cell mass. For example, the act 614 comprises draining the cell culture media 612 from the small scale adherent bioreactor. Additionally, or alternatively, separating the cell mass refers to removing the cell mass from the small scale adherent bioreactor, and thus, harvesting the cell mass by removing the cell mass from the controlled environment. In some implementations, the act 614 further comprises removing the cells from the small scale adherent bioreactor and transferring them to a harvest container such as a jacketed bag filter. For instance, a cell scraper or fluid pressure may be used to detach cells from the walls of the small scale adherent bioreactor. The cells may be kept in the small scale adherent bioreactor or transferred to a harvest container for additional processing.

As further illustrated in FIG. 6A, the disclosed method comprises an act 616 of washing the cell mass. To illustrate, a wash buffer 624 may be flowed through the bag filter holding the cell mass. Wash buffer that flows through the cell mass is discarded as waste 628. In some implementations, enrichment media 626 is also added to the cell mass.

FIG. 6A also illustrates an act 618 of drying the cell mass. Generally, the disclosed method can reduce the moisture content of the cell mass in the harvest room. In some embodiments, drying the cell mass comprises pressing the cell mass on a cell press. In other embodiments, the cells may be dried by centrifuging the cells, filtering the cells, or other means. The dried cell mass may be transferred to food production as shown by act 622. More specifically, the dried cell mass may directly proceed to food production. In other embodiments, and as shown by act 620, the dried cell mass is packaged and cold stored before proceeding to food production.

While FIG. 6A illustrates a series of acts for growing and processing adherent cells, similar acts may be performed to grow and process suspension cells. To illustrate, cells can be thawed, scaled up, and transferred to a suspension container for growth. The suspension container can comprise a tube. Cells are suspended in the cell culture media 612 in the cell culture media for a growth period. The suspension container can optionally be cold stored. The suspension container may be moved into the harvest room where cells are separated from the cell culture media by centrifugation. The suspension cells are further washed by suspending them in the wash buffer 624 and separating the cells from the wash buffer by centrifugation. The cells can be further dried, packaged, and transferred to food production.

FIG. 6A illustrates an example series of acts for small-scale cellular growth in accordance with one or more embodiments. FIG. 6B illustrates large-scale cellular growth in accordance with one or more embodiments. As illustrated in FIG. 6B, the disclosed method comprises an act 630 of thawing cells and an act 632 of scaling up the cells. As described previously, scaling up the cells comprises moving the cells and cell culture media 652 into increasingly larger containers to stimulate cellular growth. More specifically, the act 632 may be performed using a series of progressively larger flasks. In some implementations, scaling up the cells further continues in cultivators.

FIG. 6B also includes an act 634 of transferring cells to a cultivator. The cultivator may comprise an adherent reactor. As mentioned, the cells may be scaled up in a series of cultivators. For example, cells may be seeded in a small bioreactor, a medium bioreactor, and a large bioreactor after periods of growth. The cell culture media 652 is added and, in some embodiments, drained to continue feeding the cells and removing cellular waste. Used or excess cell culture media can be discarded as waste 658.

The cells seeded in the cultivator are grown as a cell mass, as shown by an act 636. In some implementations, the disclosed method comprises an act 638 of transferring the cell mass to a harvest collector. As mentioned, pressurized cell culture media 652 can be used to wash the cell mass off the substrate in the cultivator into the harvest collector.

The disclosed method illustrated in FIG. 6B further comprises an act 640 of separating the cell mass. More specifically, the act 640 comprises separating the cell mass from the cell culture media 652. In some implementations, the harvest collector comprises a filtering mechanism to separate the cell mass from the cell culture media 652.

FIG. 6B further illustrates an act 642 of washing the cell mass. For example, wash buffer 654 can be flowed through the cell mass. Excess wash buffer or wash buffer that flows through the cell mass may be discarded as waste 658, reused, or recycled. In some implementations, the cell mass is further rinsed or stored in enrichment media 656. Furthermore, the disclosed method comprises an act 644 of drying the cell mass. The cell mass may be filtered, pressed, or otherwise dried to reduce the moisture content of the cell mass.

FIG. 6B illustrates an act 646 of moving the cell mass to the harvest room. Acts that are performed below the act 646 occur in the harvest room where the cell mass is removed from the controlled environment. The act 646 may be performed after any other act illustrated in FIG. 6B. For example, the act 646 may be performed after the act 640 of separating the cell mass.

FIG. 6B illustrates an optional act 648 of packaging and cold storing the cell mass and an act 650 of transferring the cell mass to food production.

In some embodiments, the acts illustrated in FIG. 6B or similar acts are performed for large-scale cellular growth of cells grown in suspension. For example, suspension cells can be scaled up and grown in a cultivator. The cells are transferred to a harvest collector and separated from the cell culture media by centrifugation. The cells can be washed with the wash buffer by suspending the cells in the wash buffer 654 and separating the wash buffer 654 from the cells using centrifugation. The disclosed method can further reduce the moisture content of the cells by drying the cells by pressing, centrifuging, filtering, or other methods. The suspension cells can be moved to the harvest room, (optionally) packaged, and transferred to food production.

Figure 7:
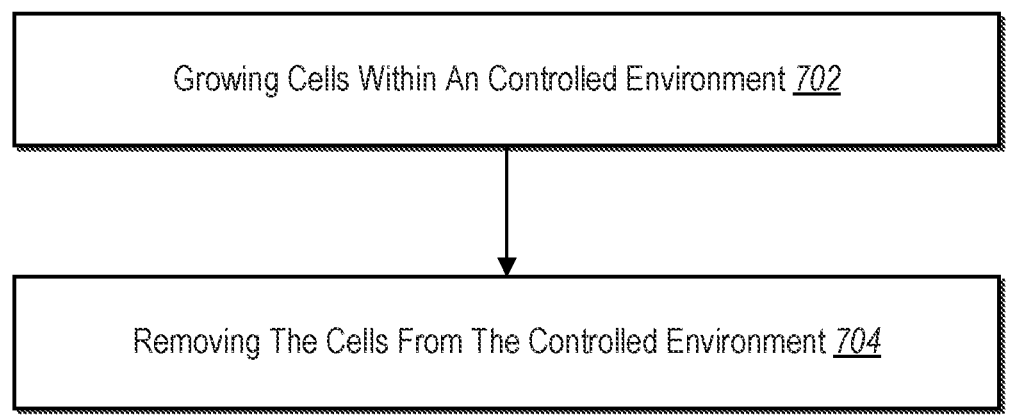
FIGS. 7, 8, and 9 illustrate series of acts for growing cells in a controlled environment, transporting the cells to a harvest room, and removing the cells from the controlled environment in accordance with one or more implementations of the present disclosure.
Figure 8:
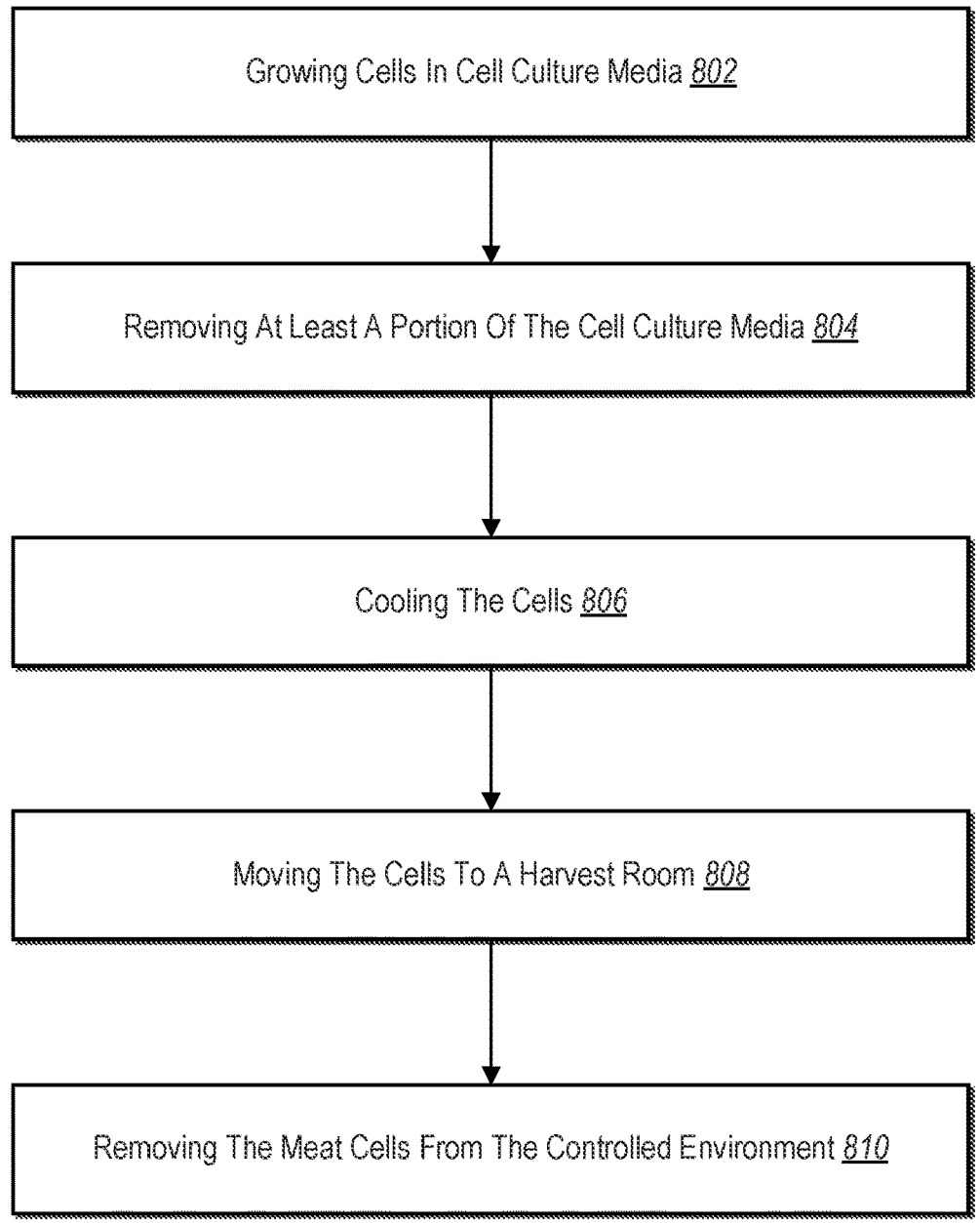
Figure 9:
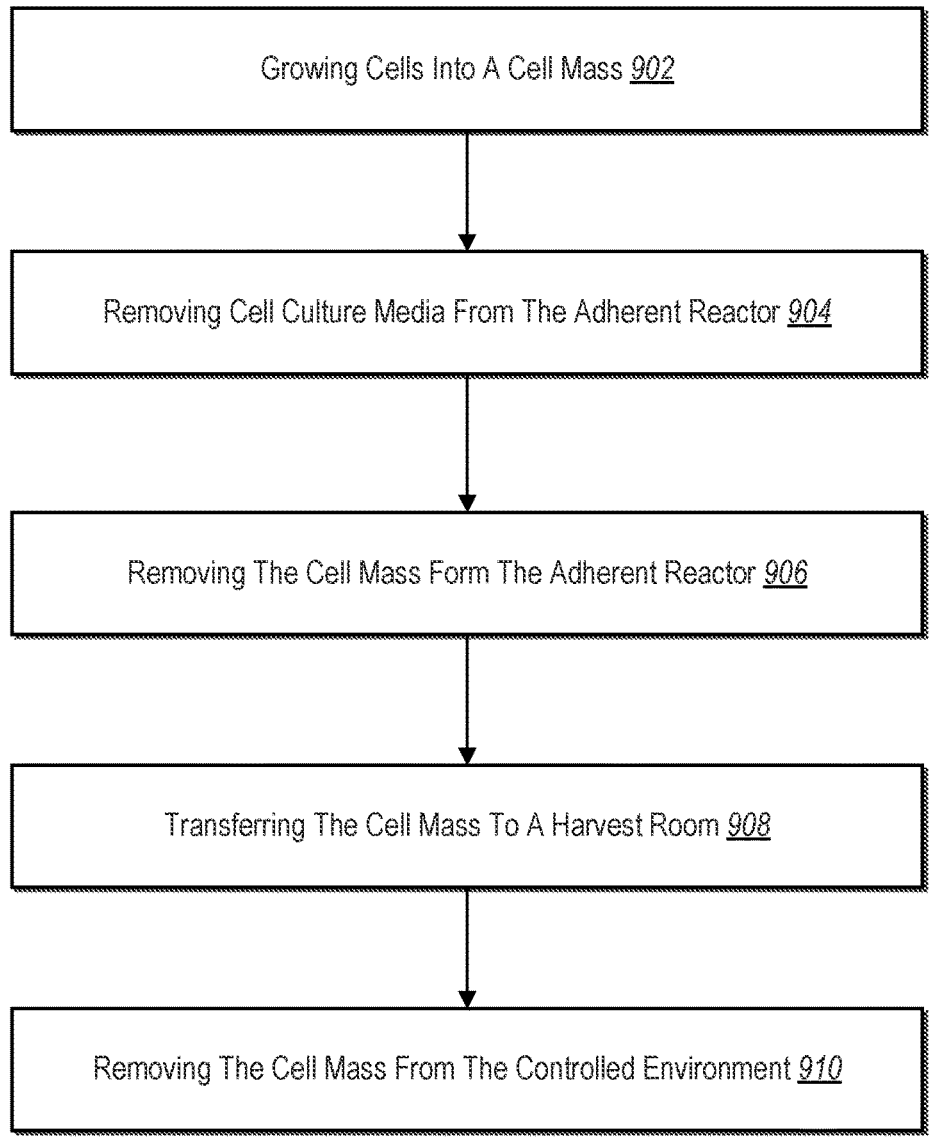

FIGS. 1-6B, the corresponding text, and the examples provide several different systems, methods, techniques, components, and/or devices relating to growing and processing cells in a controlled environment and removing the cells from the controlled environment in a harvest room in accordance with one or more implementations. In addition to the above description, one or more implementations can also be described in terms of flowcharts including acts for accomplishing a particular result. FIGS. 7-9 illustrate such flowcharts of acts. The acts described herein may be repeated or performed in parallel with one another or in parallel with different instances of the same or similar acts.

By way of overview, FIG. 7 illustrates a series of acts 700 including an act 702 of growing cells within a controlled environment and an act 704 of removing the cells from the controlled environment.

The series of acts 700 includes the act 702 of growing cells within a controlled environment. In particular, the act 702 comprises growing cells comprising mesenchymal progeny in a cultivator within a controlled environment, wherein the cultivator is housed in a growing room. In some implementations, the series of acts 700 comprises growing the cells in the cultivator at a temperature of 95 degrees Fahrenheit. In some implementations, the cells comprise cells grown in suspension. In some implementations, the cells grow into a cell mass and the cultivator comprises an adherent reactor.

FIG. 7 further illustrates the act 704 of removing the cells from the controlled environment. In particular, the act 704 comprises removing the cells from the controlled environment in a harvest room. In some implementations, the harvest room comprises a clean room having a low concentration of airborne particulates. In some implementations, the harvest room is kept at refrigeration temperatures between 35- and 44-degrees Fahrenheit. In some implementations, the harvest room does not share airflow with the growing room that houses the cultivator. Furthermore, in some implementations, a door between the growing room and the harvest room comprises an equipment-only door.

In some implementations, the series of acts 700 comprises an additional act of transferring the cells from the cultivator into a harvest collector within the controlled environment, and moving the harvest collector to the harvest room prior to removing the cells from the controlled environment. Furthermore, in some implementations, the additional act further comprises cooling the cells to a temperature of between 32 and 41 degrees Fahrenheit before moving the harvest collector to the harvest room.

FIG. 8 illustrates a series of acts 800 comprising an act 802 of growing cells in cell culture media, an act 804 of removing at least a portion of the cell culture media, an act 806 of cooling the cells, an act 808 of moving the cells to a harvest room, and an act 810 of removing the cells from the controlled environment.

As illustrated in FIG. 8, the series of acts 800 comprises the act 802 of growing cells in cell culture media. In particular, the act 802 comprises growing cells comprising mesenchymal progeny in cell culture media in a controlled environment, wherein the cells are grown in suspension.

The series of acts 800 includes the act 804 of removing at least a portion of the cell culture media. The act 804 comprises removing at least a portion of the cell culture media from the cells in the controlled environment. In some implementations, the act 804 further comprises removing the portion of the cell culture media from the cells by centrifuging the cells and the cell culture media.

The series of acts 800 illustrated in FIG. 8 also includes the act 806 of cooling the cells. The act 806 comprises cooling the cells in the controlled environment.

The series of acts 800 includes the act 808 of moving the cells to a harvest room. In particular, the act 808 comprises moving the cells to a harvest room by utilizing a transfer mechanism within the controlled environment.

FIG. 8 further illustrates the act 810 of removing the cells from the controlled environment. In particular, the act 810 comprises removing the cells from the controlled environment in the harvest room.

The series of acts 800 further comprises an act of centrifuging the cells to reduce liquid content before removing the cells from the controlled environment. Additionally, the series of act 800 may further comprise an act of cooling the cells by rinsing the cells with a cooled wash buffer.

Furthermore, in some instances, the series of acts 800 further comprises an act of washing the cells by: rinsing the cells in a wash buffer in the controlled environment; and centrifuging the wash buffer and the cells to remove the wash buffer.

FIG. 9 illustrates a series of acts 900 comprising an act 902 of growing cells into a cell mass, an act 904 of removing cell culture media from the adherent reactor, an act 906 of removing the cell mass from the adherent reactor, an act 908 of transferring the cell mass to a harvest room, and an act 910 of removing the cell mass from the controlled environment.

The series of acts 900 comprises the act 902 of growing cells into a cell mass. In particular, the act 902 comprises growing cells into a cell mass in an adherent reactor in a controlled environment.

The series of acts 900 includes the act 904 of removing cell culture media from the adherent reactor. In particular, the act 904 comprises removing cell culture media from the adherent reactor in the controlled environment.

FIG. 9 further illustrates the act 906 of removing the cell mass from the adherent reactor. In particular, the act 906 comprises removing the cell mass from the adherent reactor in the controlled environment. In some implementations, the act 906 comprises spraying cell media across a substrate in the adherent reactor to release the cell mass from the substrate and collecting the cell media and the cell mass in a harvest collector. In some implementations, the cell media comprises the cell culture media that was removed from the adherent reactor. Furthermore, in some implementations, the harvest collector comprises a filter mechanism to separate the cell media from the cell mass.

The series of acts 900 further includes the act 908 of transferring the cell mass to a harvest room. In particular, the act 908 comprises transferring the cell mass to a harvest room while maintaining the controlled environment.

FIG. 9 also illustrates the act 910 of removing the cell mass from the controlled environment. In particular, the act 910 comprises removing the cell mass from the controlled environment in the harvest room.

In some implementations, the series of acts 900 further comprises washing the cell mass by rinsing the cells in a wash buffer in the controlled environment and filtering the wash buffer and the cells to remove the wash buffer in the controlled environment.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various implementations of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to implementations containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to implementations containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absent a showing that the terms "first," "second," "third," etc., connote a specific order, these terms should not be understood to connote a specific order. Furthermore, absent a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art and are to be construed as being without limitation to such specifically recited examples and conditions. Although implementations of the present disclosure have been described in detail, it should be understood that the various changes, substitutions, and alterations could be made hereto without departing from the spirit and scope of the present disclosure.

The present invention may be embodied in other specific forms without departing from its spirit or essential characteristics. Indeed, the described implementations are to be considered in all respects only as illustrative and not restrictive. For example, the methods described herein may be performed with less or more steps/acts or the steps/acts may be performed in differing orders. Additionally, the steps/acts described herein may be repeated or performed in parallel to one another or in parallel to different instances of the same or similar steps/acts. The scope of the invention is, therefore, indicated by the appended claims rather than by the foregoing description. All changes that come within the meaning and range of equivalency of the claims are to be embraced within their scope.

What is claimed is:

1. A method for producing a comestible cell-based meat product comprising:
   growing non-human cells comprising non-human mesenchymal progeny in a cultivator within a controlled environment, wherein the cultivator is housed in a growing room;
   transferring the non-human cells from the growing room to a harvest room while maintaining the controlled environment; and
   harvesting the non-human cells by removing the non-human cells from the controlled environment and first exposing the non-human cells to air outside of the controlled environment while in the harvest room.

2. The method of claim 1, wherein the harvest room is kept at refrigeration temperatures between 35 and 44 degrees Fahrenheit.

3. The method of claim 1, wherein the harvest room does not share airflow with the growing room that houses the cultivator.

4. The method of claim 1, wherein a door between the growing room and the harvest room comprises an equipment-only door.

5. The method of claim 1, wherein transferring the non-human cells from the growing room to the harvest room while maintaining the controlled environment comprises transferring the non-human cells from the growing room to the harvest room in into a harvest collector that maintains the controlled environment.

6. The method of claim 5, further comprising cooling the non-human cells to a temperature of between 32 and 41 degrees Fahrenheit before moving the harvest collector to the harvest room.

7. The method of claim 1, further comprising growing the non-human cells in the cultivator at a temperature of 95 degrees Fahrenheit.

8. The method of claim 1, wherein the harvest room comprises a clean room having a low concentration of airborne particulates.

9. The method of claim 1, wherein the non-human cells comprise non-human cells grown in suspension.

10. The method of claim 1, wherein:
    the non-human cells grow into a cell mass; and
    the cultivator comprises an adherent reactor.

11. A method for producing a comestible cell-based meat product comprising:
    growing non-human cells comprising non-human mesenchymal progeny in cell culture media in a controlled environment;
    removing at least a portion of the cell culture media from the non-human cells in the controlled environment;
    cooling the non-human cells in the controlled environment;

moving the non-human cells to a harvest room by utilizing a transfer mechanism that maintains the non-human cells within the controlled environment; and harvesting the non-human cells by removing the non-human cells from the controlled environment and exposing the non-human cells to air outside of the controlled environment while in the harvest room.

12. The method of claim 11, further comprising centrifuging the non-human cells to reduce liquid content prior to harvesting the non-human cells.

13. The method of claim 11, further comprising cooling the non-human cells by rinsing the non-human cells with a cooled wash buffer.

14. The method of claim 11, further comprising removing the portion of the cell culture media from the non-human cells by centrifuging the non-human cells and the cell culture media.

15. The method of claim 11, further comprising washing the non-human cells by:

rinsing the non-human cells in a wash buffer in the controlled environment; and centrifuging the wash buffer and the non-human cells to remove the wash buffer.

16. A method for producing a comestible cell-based meat product:

growing non-human cells into a cell mass in an adherent reactor in a controlled environment;

removing cell culture media from the adherent reactor in the controlled environment;

transferring the cell mass from the adherent reactor to a harvest room while maintaining the controlled environment; and harvesting the cell mass by removing the cell mass from the controlled environment and exposing the cell mass to air outside of the controlled environment while in the harvest room.

17. The method of claim 16, further comprising removing the cell mass from the adherent reactor by:

spraying cell media across a substrate in the adherent reactor to release the cell mass from the substrate; and collecting the cell media and the cell mass in a harvest collector.

18. The method of claim 16 further comprising washing the cell mass by:

rinsing the non-human cells in a wash buffer in the controlled environment; and filtering the wash buffer and the non-human cells to remove the wash buffer in the controlled environment.

19. The method of claim 17, wherein the cell media comprises the cell culture media that was removed from the adherent reactor.

20. The method of claim 17, wherein the harvest collector comprises a filter mechanism to separate the cell media from the cell mass.

* * * * *